United States Patent

Wasleski et al.

[11] Patent Number: 5,877,339
[45] Date of Patent: Mar. 2, 1999

[54] PROCESS FOR PREPARING METHYL DITHIOCARBAZINATE BY REACTING METHYL BROMIDE WITH THE REACTION PRODUCT OF CARBON DISULFIDE AND HYDRAZINE IN AN AQUEOUS MEDIUM

[75] Inventors: Daniel M. Wasleski, Blue Springs, Mo.; Peter E. Newallis, Leawood; Dennis E. Jackman, Prairie Village, both of Kans.; David T. Erdman, Köln, Germany; Jeffrey D. Macke, Kansas City, Mo.; Vidyanatha A. Prasad, Leawood; Vijay C. Desai, Shawnee, both of Kans.

[73] Assignee: Bayer Corporation, Pittsburgh, Pa.

[21] Appl. No.: 743,764

[22] Filed: Nov. 7, 1996

[51] Int. Cl.$^6$ .................................................. C07C 337/02
[52] U.S. Cl. ............................................... 558/233
[58] Field of Search ................................................ 558/233

[56] References Cited

U.S. PATENT DOCUMENTS

| | | | |
|---|---|---|---|
| 2,914,547 | 11/1959 | Gaertner | 558/233 |
| 3,261,858 | 7/1966 | D'Amico | 558/233 |
| 3,284,482 | 11/1966 | D'Amico et al. | 260/455 |
| 3,388,146 | 6/1968 | Halasa | 558/233 |
| 4,696,938 | 9/1987 | Le | 514/343 |

FOREIGN PATENT DOCUMENTS

| | | |
|---|---|---|
| 0 602 589 | 6/1994 | European Pat. Off. . |
| 1274521 | 5/1972 | United Kingdom . |

OTHER PUBLICATIONS

Sandström et al, Arkiv För Kemi, 4(1952), p. 297.
Audrieth et al., J. Organic Chem., vol. 19, pp. 733–741 1954.
S. Losanitch, J. Chem. Soc., vol. 119, pp. 763–765 1921.

*Primary Examiner*—Michael G. Ambrose
*Attorney, Agent, or Firm*—Joseph C. Gil; Godfried R. Akorli; Carol Marmo

[57] ABSTRACT

Disclosed herein is an aqueous process for preparing high yields of methyl dithiocarbazinate by reacting carbon disulfide and hydrazine in an effective ratio, in an aqueous medium to form hydrazinium dithiocarbazinate salt followed by methylating the hydrazinium dithiocarbazinate with methyl bromide.

9 Claims, No Drawings

PROCESS FOR PREPARING METHYL DITHIOCARBAZINATE BY REACTING METHYL BROMIDE WITH THE REACTION PRODUCT OF CARBON DISULFIDE AND HYDRAZINE IN AN AQUEOUS MEDIUM

BACKGROUND OF THE INVENTION

1. Field of the Invention

The present invention relates to an improved process for preparing methyl dithiocarbazinate. In particular, the present invention relates to an economical process for preparing methyl dithiocarbazinate by reacting hydrazine with carbon disulfide.

2. Brief Description of the Prior Art

Illustrative of the prior art of preparing methyl dithiocarbazinate are the following: Audrieth et al., J. Organic Chem., Vol. 19, pp. 733–741 (1954) discloses a process for preparing methyl dithiocarbazinate and converting it to thiocarbohydrazide. The process comprises a dropwise addition of 1.04 moles of carbon disulfide to 1.18 moles of potassium hydroxide and 1.1 moles of 85% hydrazine in 200 ml. of ethanol, in an ice bath. A heavy yellow oil containing potassium dithiocarbazinate separates during the addition. The resulting mixture is stirred and chilled and two volumes of ether are added to cause separation of more of the desired product (potassium dithiocarbazinate).

The oily layer is separated from the ether-alcohol layer and filtered to remove a small amount of an unidentified solid that is formed. The clear yellow solution is then dissolved in 300 ml. of water. The resulting solution is cooled in an ice bath and 1.05 moles of methyl iodide are added in approximately 10 batches. The reaction vessel is shaken and cooled alternately after each such addition until the methyl iodide is consumed. The reaction mixture is allowed to stand for several hours, being shaken occasionally to permit complete reaction. The methyl dithiocarbazinate is collected and recrystallized from ethanol.

Methyl dithiocarbazinate (24.4 g, 0.2 mole) was dissolved in 200 ml. of absolute ethanol and 18 ml. (0.3 mole of hydrazine) of 85% hydrazine hydrate was added. The resulting solution was refluxed until no more solid thiocarbohydrazide precipitated (about 45 minutes). A small amount of 3-hydrazino-4-amino-5-mercapto-1,2,4-triazole that had formed was removed as follows: The reaction mixture was chilled, and the resulting solid product was collected and recrystallized from water acidified with a few drops of hydrochloric acid.

Le, U.S. Pat. No. 4,696,938 discloses a process for preparing and using methyl hydrazinecarbodithioate as an intermediate in the preparation of 6-aryl-pyridine thiosemicarbazones. Methyl dithiocarbazinate is prepared as follows: Hydrazine hydrate (150 g) is added to a cooled (0° C.) solution of potassium hydroxide in water (240 ml.) and 2-propanol (200 ml.). Pre-cooled carbon disulfide (182 ml.) is then added dropwise to the stirred reaction mixture, while maintaining an internal temperature below 10° C. After the addition is complete, stirring is continued for a further one hour. Cooled methyl iodide (426 g) is added dropwise over 1% hours. The resulting white precipitate is collected by filtration and washed with cooled water. The crude product is recrystallized from methylene chloride.

To form 6-aryl-pyridine thiosemicarbazone, methyl dithiocarbazinate is reacted in a suitable solvent such as alcohol. The reaction product is treated with selenium dioxide in a suitable ethereal solvent such as tetrahydrofuran or 1,4-dioxane.

S. Losanitch, J. Chem. Soc., Vol. 119, pp. 763–765 (1921) discloses a process for preparing methyl dithiocarbazinate by first obtaining ammonium dithiocarbazinate and reacting it with methyl iodide. The ammonium dithiocarbazinate is obtained as follows: A solution of hydrazine hydrate in alcohol, containing a large excess of ammonia, is slowly treated with cooling with the corresponding quantity of carbon disulfide. The methyl dithiocarbazinate is formed by treating the ammonium salt in a dilute alcohol solution with methyl iodide.

Sandstrom et al, Arkly For Kemi, 4(1952) 297, discloses a process for preparing ethyl dithiocarbazinate. The process involves the separation of hydrazinium dithiocarbazinate from an ethanol-water mixture and the reaction of the hydrazinium dithiocarbazinate with ethyl bromide in an ethanol-water mixture.

U.S. Pat. No. 3,284,482 discloses a process for preparing chlorobenzyl esters of dithiocarbazinic acid as follows: To a solution comprising 85% hydrazine, 25% sodium hydroxide and 300 ml. of water is added carbon disulfide, dropwise at 10° to 15° C. over 20 minutes. External cooling is removed and the reaction mixture is stirred for an hour at 25° to 30° C. Then, trichlorobenzyl chloride is added in one portion to the reaction mixture which is stirred for 24 hours at 25° to 30° C. to produce the corresponding trichlorobenzyl dithiocarbazinate. The product is then extracted with ethyl ether. The ether solution is washed with water until it becomes neutral, is dried over sodium sulfate, and the ether is removed in vacuo.

British Patent Specification 1,274,521 discloses dithiocarbazinic ester derivatives by reacting dithiocarbazinic acid esters with an oxo compound. The dithiocarbazinic acid is prepared by reacting hydrazine hydrate with carbon disulfide in alcohol medium in the presence of potassium hydroxide, ammonia or excess hydrazine hydrate.

After isolation, the dithiocarbazinic acid salt is converted into an ester via an alkylating or aralkylating step. This step is carried out in water, a mixture of water and alcohol or in alcohol. Alternately, the ester can be prepared in a single reactor. The alkylating or aralkylating agent is added to the dithiocarbazinic acid salt solution prepared by the above method. The alkylating or aralkylating agents disclosed by the patent are: dimethyl sulfate, diethyl sulfate, allyl chloride, n-butyl iodide, n-octyl ester, n-dodecyl bromide, cetyl bromide, benzyl chloride, p-chlorobenzyl chloride, p-isopropylbenzyl bromide, p-n-butylbenzyl bromide and alphamethylbenzyl chloride.

As would be realized from the foregoing, there is a need for an economic process, i.e., a more facile and cost efficient process for preparing methyl dithiocarbazinate. In particular, there is a need for a more economic commercial process for preparing methyl dithiocarbazinate. By the present invention, there is provided such an improved process for preparing methyl dithiocarbazinate.

SUMMARY OF THE INVENTION

Surprisingly, it has been found that methyl dithiocarbazinate can be prepared by a facile and cost effective process comprising: reacting hydrazine and carbon disulfide in an effective ratio in an aqueous reaction medium to form a hydrazinium dithiocarbazinate salt, followed by reacting (methylating) the dithiocarbazinate salt with methyl bromide.

In the present embodiment of the invention, 1 mole of carbon disulfide is reacted with at least 2 moles of hydrazine in a reaction medium comprising water, and a non-aqueous solvent such as toluene. The resulting reaction mixture comprising hydrazinium dithiocarbazinate is reacted with methyl bromide to produce high yields of methyl dithiocarbazinate.

In contrast, art-related processes generally involve the reaction of carbon disulfide and hydrazine in a reaction medium containing alcohols; separation of the resulting dithiocarbazinate; the use of relatively more expensive or more intractable and sometimes commercially cost prohibitive alkylating agents such as methyl iodide; and catalysts such as sodium iodide, and/or recrystallization of the resulting methyl dithiocarbazinate.

It is a distinct feature of the invention that one can eliminate the use of undesirable methylating agents such as methyl iodide, undesirable solvents such as alcohols, and expensive catalysts such as sodium iodide. It is a distinct feature of the invention that the process requires short reaction times, requires no isolation of intermediate dithiocarbazinate salts, and no recrystallization of the final methyl dithiocarbazinate. Consonantly, the process of the invention fills a long felt but unmet need of using a facile process for preparing methyl dithiocarbazinate by using readily available and relatively less expensive reactants and solvents, and processing techniques.

In the practice of the invention, methyl dithiocarbazinate can be used as an intermediate compound in the preparation of other chemicals such as thiadiazoles.

DETAILED DESCRIPTION OF THE INVENTION

As afore-stated, the claimed invention relates to a process for preparing methyl dithiocarbazinate by: reacting hydrazine (typically as hydrazine hydrate) with carbon disulfide in an effective ratio, in an aqueous reaction medium to form hydrazinium dithiocarbazinate, followed by methylating the hydrazinium dithiocarbazinate with methyl bromide. The process can be represented by reactions (I) and (II), as follows:

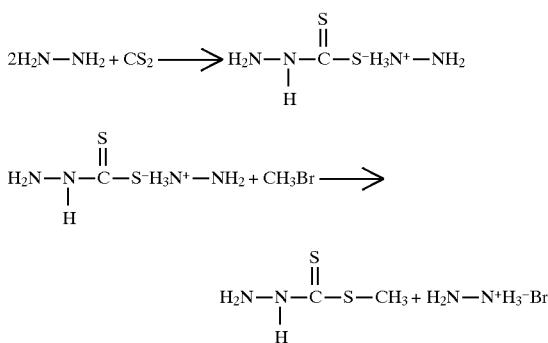

As set forth above, hydrazine and carbon disulfide are employed as the starting materials in reaction (I). Hydrazine is typically employed in the form of hydrazine hydrate, and carbon disulfide is typically employed in the form of a liquid. As the effective ratio, one can employ hydrazine and carbon disulfide in a mole ratio of about 4 to 2:1 and preferably 2.4:1. As the reaction medium, one can employ water as the principal reaction vehicle, preferably in combination with a non-aqueous solvent which is an aprotic solvent. The mole ratio of water to carbon disulfide can be about 5 to 20:1 and preferably 10 to 20:1. The aprotic solvent is non-alcoholic and is preferably a hydrocarbon solvent. As the hydrocarbon solvent, one can use an aliphatic hydrocarbon solvent selected from the group consisting of alkanes such as pentane, hexane, and heptane. Also, one can employ an aromatic hydrocarbon selected from the group consisting of toluene (which is preferred), benzene and xylene. The solvent can be employed in a mole ratio of about 0.15 to 1 mole per mole of carbon disulfide. Unlike the reaction medium of many of the prior art processes, the aqueous reaction medium of this invention need not contain alcoholic solvents. In this regard, the reaction medium consists essentially of water, and an aprotic solvent.

The following reaction conditions can be employed in reaction (I). The reaction can be about –5° to 35° C. and preferably 10° to 25° C., for about 1 to 4 hours and preferably 1 to 2 hours at a pH of about 8 to 14 and preferably 9 to 14. The resulting reaction product comprises hydrazinium dithiocarbazinate.

In reaction (II), the reaction product comprising hydrazinium dithiocarbazinate is reacted with methyl bromide. The mole ratio of methyl bromide to hydrazinium dithiocarbazinate can be from about 1.5 to 1:1, about 1.5 to 1.02:1, and preferably 1.05:1. While reaction (II) can be conducted in another reaction vessel, it is typically conducted in the same reaction vessel as used in reaction (I). The reaction medium employed in reaction (II) is essentially the same as that of reaction (I). Water can be employed in a mole ratio of 20 to 5 and preferably 15 to 5 per mole of hydrazinium dithiocarbazinate. The solvent employed here is essentially the same as the solvent of reaction (I). The solvent can be employed in a mole ratio of 0 to 3 and preferably 0.1 to 1.0 mole per mole of hydrazinium dithiocarbazinate. Reaction (II) can be conducted at a pH range of about 8 to 14 and preferably 9 to 14, at a temperature of about 0° to 35° C. and preferably 5° to 25° C., for about 0.5 to 3 hours and preferably 1 to 2 hours.

It is a distinct feature of the invention that the methylation reaction can be conducted without isolating the dithiocarbazinate salts of reaction (I). Accordingly, the methylation reaction (II) consists essentially of reacting the reaction product of reaction (I) with methyl bromide. It is also a distinct feature of the invention that the methylating reaction (II) can be conducted without the use of expensive reaction catalysts such as sodium iodide. Accordingly, the methylating step consists essentially of reacting the reaction product of (I) with methyl bromide. Alternately, the hydrazinium dithiocarbazinate can be isolated by, say, filtration and subsequently reacted with methyl bromide. Illustratively, the hydrazinium dithiocarbazinate can be filtered, slurried in a reaction medium such as described above, and then reacted with methyl bromide. The reaction conditions would be essentially the same as described above.

The resulting product containing methyl dithiocarbazinate can be isolated by any convenient means. Illustratively, methyl dithiocarbazinate can be isolated as a wet cake by filtering or centrifuging. The methyl dithiocarbazinate can be collected on a vacuum filter and washed with water to remove impurities such as hydrazinium hydrobromide. The resulting cake can be used as such in subsequent reactions. Alternately, it can be dried by any means that is effective to provide the requisite drying without causing decomposition of the product. Illustratively, the product can be dried by exposing it to temperatures that do not cause decomposition of the products. More specifically, the product can be dried in a vacuum oven, using a nitrogen sparge at a temperature of about 30° C. to 40° C. Generally, the resultant methyl dithiocarbazinate purity can be up to about 95 percent with variation attributable to washing and/or drying steps.

As would be realized from the above, methyl dithiocarbazinate can be obtained without recrystallization of the reaction product of reaction (II). Accordingly, methyl dithiocarbazinate can be prepared by a process consisting essentially of reacting carbon disulfide and hydrazine in an aqueous medium in an effective ratio to form a dithiocarbazinate salt, followed by methylating the dithiocarbazinate salt with methyl bromide, and removing impurities such as the bromide salt. It is a distinct feature of the invention that the process consists essentially of preparing the hydrazinium dithiocarbazinate and methylating it without separating it from the reaction medium.

A catalyst, typically a phase transfer catalyst such as n-benzyl-trimethylammonium hydroxide, can be employed in the reaction(s). Other catalysts useful herein can be selected from the group consisting of tris[2-(2-methylethoxy) ethyl] amine (TDA-1), N-methylimidazole, dimethylaminopyridine, 1,4-diazabicyclo (2,2,2) octane diglyme (2-methoxymethylether) and diethylene glycol. The mole ratio of the catalyst can be about 10 percent and preferably about 2 percent per mole of carbon disulfide. Other reaction adjuncts can be employed in the reactions.

The following is a convenient but non-limiting illustration of the process for preparing methyl dithiocarbazinate in accordance with this invention. Hydrazine hydrate is added slowly to a mixture of toluene and water at a temperature below 25° C. Carbon disulfide is then added dropwise to the reaction mixture while maintaining the temperature at 25° C. Once the resulting hydrazinium dithiocarbazinate begins to precipitate, the reaction mixture turns into a slurry and usually remains as such in the subsequent methylating reaction. In the methylation reaction, methyl bromide is then added to the reaction mixture over a period of about 2 hours at 25° C. The reaction mixture is agitated for about an hour at 25° C.; cooled to 0 to 5° C.; filtered and dried. The yield of the resultant methyl dithiocarbazinate can be from about 77 to 90 percent.

The following are specific but non-limiting examples of the invention. Unless otherwise specified, all parts and percentages hereunder are by weight.

EXAMPLES

Example 1

This example illustrates the preparation of methyl dithiocarbazinate (MDTC) in accordance with the invention as follows. In a properly equipped reaction vessel (four-neck, 1000 ml. flask equipped with a thermometer, an overhead stirrer, Dewar condenser, an equalizing addition funnel and a gas dispersion tube) hydrazine hydrate (150.0 g, 3.00 mol.) was slowly added (with cooling) to a mixture of toluene (43.25 g, 0.46 moles) and water (264 g, 14.6 moles) at <25° C. Carbon disulfide (114.0 g, 1.50 mol.) was then added (1 hour) to the above mixture while maintaining the temperature at 25° C. Thereafter, methyl bromide (156.7 g, 1.65 mol.) was introduced into the reaction vessel over a period of 2 hours at 25° C. The mixture was agitated for 1 hour at 25° C., cooled to 0° to 5° C., and the solids were filtered and dried (overnight at 40° C./20 mm) to yield 159.3 g (84.5%) of white solid. The mother liquor contained an additional 3 to 5% of MDTC.

Example 2

This example illustrates the preparation of methyl dithiocarbazinate (MDTC) without using toluene. In a properly equipped reaction vessel, hydrazine hydrate (150.0 g, 3.00 mol.) was slowly added (with cooling) to water (264 g, 14.6 mol.) at <25° C. Carbon disulfide (114.0 g, 1.50 mol.) was then added (1 hour) to the above mixture while maintaining the temperature, and methyl bromide (156.7 g, 1.65 mol.) was introduced over a period of 2 hours at 25° C. The mixture was agitated for 1 hour at 25° C., cooled to 0° to 5° C., and the solids were filtered and dried (overnight at 40° C./ 20 mm) to yield 80% of white solid (purity 91%). The mother liquor contained an additional 3 to 5% of MDTC.

Although the invention has been described in detail in the foregoing for the purpose of illustration, it is to be understood that such detail is solely for that purpose, and that variations can be made therein by those skilled in the art without departing from the spirit and scope of the invention except as it may be limited by the claims.

What is claimed is:

1. A process for preparing methyl dithiocarbazinate comprising:

a) reacting carbon disulfide and hydrazine in an aqueous medium in an effective ratio to form a hydrazinium dithiocarbazinate, and, without isolating said hydrazinium dithiocarbazinate, b) methylating said hydrazinium dithiocarbazinate in the same aqueous medium with methyl bromide, wherein said aqueous medium is selected from the group consisting of water and a mixture of water and an aprotic solvent, provided that when said aqueous medium is a mixture of water and an aprotic solvent, said aprotic solvent is used in a molar ratio of from about 0.15 to 1 mole per mole of carbon disulfide.

2. The process of claim 1 wherein said aqueous medium is water.

3. The process of claim 1 wherein said aqueous medium is a mixture of water and an aprotic solvent.

4. The process of claim 3, wherein said solvent is an aliphatic or aromatic hydrocarbon solvent.

5. The process of claim 4, wherein said solvent is selected from the groups consisting of toluene, xylene, hexane, heptane and cyclohexane.

6. The process of claim 5, wherein said solvent is toluene.

7. The process of claim 1, wherein the mole ratio hydrazine to carbon disulfide is from 4:1 to 2:1 and the mole ratio of methyl bromide to hydrazinium dithiocarbazinate is from 1.5:1 to 1:1.

8. The process of claim 1, wherein the methylation reaction is followed by isolating said methyl dithiocarbazinate as a wet cake by filtering or centrifuging.

9. The process of claim 8, further comprising drying the isolated methyl dithiocarbazinate.

* * * * *